Figure 1:
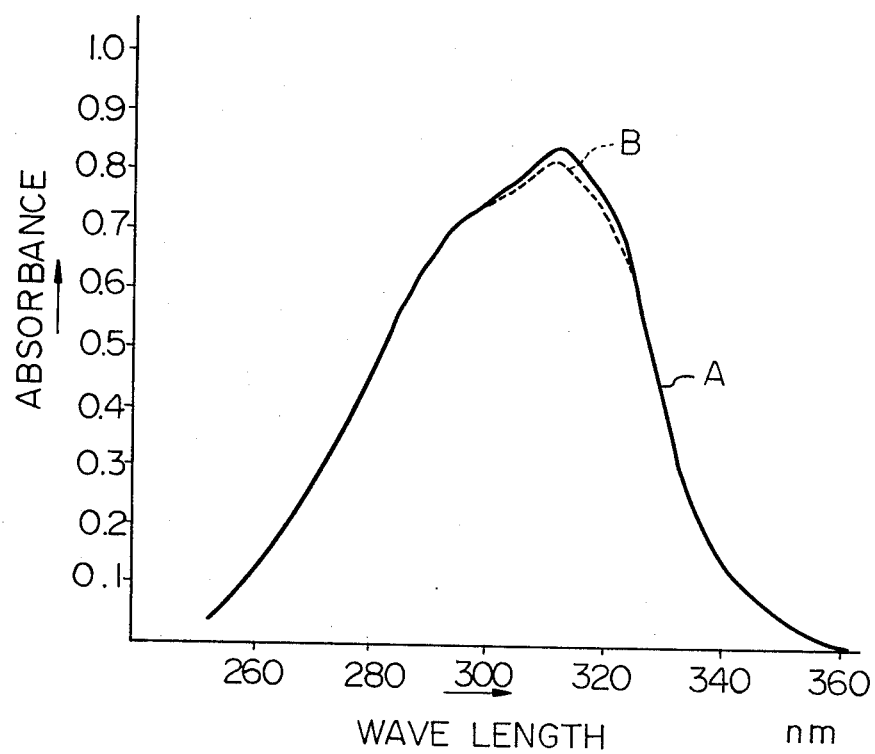

United States Patent [19]

Okazaki et al.

[11] 4,322,544
[45] Mar. 30, 1982

[54] ULTRAVIOLET ABSORBING AGENT

[75] Inventors: Tomomi Okazaki, Yokohama; Kenichi Tomita, Tokyo; Hakuji Katsura, Yokohama; Masayuki Tejima, Yokohama; Masako Naganuma, Yokohama, all of Japan

[73] Assignee: Toray Industries, Inc., Nihonbashi-Muromachi, Japan

[21] Appl. No.: 134,481

[22] Filed: Mar. 27, 1980

[30] Foreign Application Priority Data

Apr. 2, 1979 [JP] Japan ................................ 54-39614

[51] Int. Cl.³ .............................................. C07C 69/76
[52] U.S. Cl. ...................................... 560/55; 560/104; 260/410.6; 260/410.7; 424/308
[58] Field of Search ................ 560/55, 104; 260/410.6, 260/410.7, 45.85 P, 45.85 V, 45.85, E, 45.85 B; 424/308

[56] References Cited

U.S. PATENT DOCUMENTS 2,336,223 12/1943 Coleman et al. .................... 560/104
3,988,446 10/1976 Pans ..................................... 560/55

FOREIGN PATENT DOCUMENTS 17221 of 1890 United Kingdom .................. 560/71
28247 of 1911 United Kingdom .

*Primary Examiner*—Paul J. Killos
*Attorney, Agent, or Firm*—Austin R. Miller

[57] ABSTRACT

Ultraviolet absorbing compounds having the following formaulae are presented.

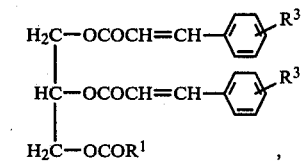

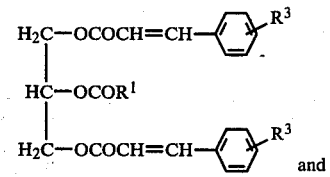

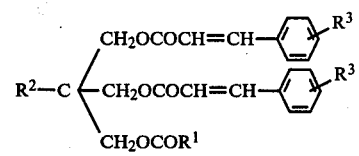

and wherein $R^1$ is a saturated branched alkyl group having 7 carbon atoms, $R^2$ is methyl or ethyl group and $R^3$ is ortho-or para- methoxy group. These compounds have good ultraviolet protective properties and cause little or no irritation to human skin.

16 Claims, 1 Drawing Figure

ULTRAVIOLET ABSORBING AGENT

The present invention relates to an ultraviolet absorbing agent and, more specifically, relates to novel methoxy cinnamic acid esters highly suitable for use, as an ultraviolet absorbing agent, in the protection of, for example, plastics, fibers and human skin against the harmful effects of ultraviolet light.

It is well-known in the art that various kinds of ultraviolet absorbing agents are incorporated into materials such as plastics, fibers and the like to protect the materials against the deterioration of the materials due to ultraviolet radiation, such as, for example, the occurrence of cracks, a decrease in the strength, discoloring, fading and the like. Furthermore, ultraviolet absorbing agents are also used in the cosmetics art for the purpose of absorbing sun light having a wave length of 290 through 320 nm, which is harmful to human skin, so that skin irritation or inflammation is prevented.

The lower alcohol esters of p-methoxy cinnamic acid, such as p-methoxy cinnamic acid 2-ethylhexyl ester and p-methoxy cinnamic acid ethoxy ethyl ester, are known as effective ultraviolet absorbing agents. However, since the molecular weight of these esters is relatively small, these esters have an unpreferable irritating effect on human skin to some extents. Contrary to this, although the irritating effect on human skin is improved by the use of the higher alcohol esters of p-methoxy cinnamic acid having a relatively high molecular weight, the ultraviolet absorbing effects of these higher alcohol esters are remarkably smaller than those of the lower alcohol esters.

Furthermore, the glycol diesters of p-methoxy cinnamic acid, such as ethylene glycol ester and propylene glycol ester of p-methoxy cinnamic acid, have high ultraviolet absorbing effects. However, since these glycol diesters of p-methoxy cinnamic acid are solid at ordinary temperature, the utility of these glycol esters, as an ultraviolet absorbing agent, is limited due to the fact that the compatibility thereof to base components or materials is not good.

Accordingly, an object of this invention is to obviate the afore-mentioned problem of the prior art and to provide an ultraviolet absorbing agent having both good ultraviolet absorbing effect and causing little or no irritation to human skin.

Other objects and advantages of this invention will be apparent from the description set forth hereinbelow.

In accordance with the present invention, there is provided an ultraviolet absorbing agent comprising at least one compound having the following general formulae:

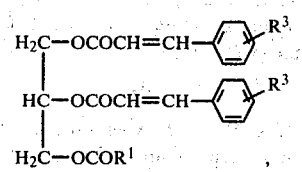

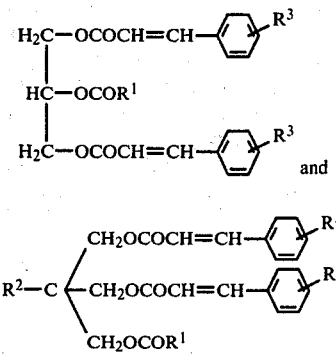

wherein $R^1$ is a saturated branched alkyl group having 7 carbon atoms, $R^2$ is a methyl or ethyl group and $R^3$ is an ortho- or para-methoxy group.

The present invention now will be illustrated in detail with reference to the accompanying drawing wherein:

FIG. 1 illustrates the absorbtion spectra of the compounds A and B (0.001% ethanol solution) in the ultraviolet region, wherein A represents glycerol mono 2-ethylhexanoyl di(p-methoxy cinnamate) having the formula:

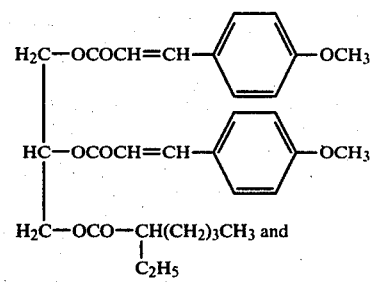

B represents a trimethylol propane mono 2-ethylhexoyl di(p-methoxy cinnamate) having the formula.

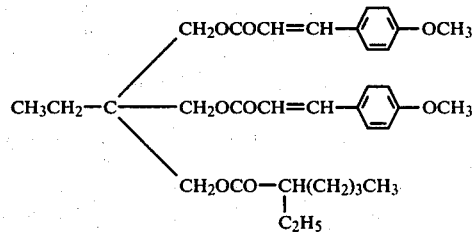

The ultraviolet absorbing compounds of the present invention having the above mentioned general formulae are, for example, (a) glycerol mono 2-ethylhexanoyl di(p-methoxy cinnamate), (b) trimethylol propane mono 2-ethylhexanoyl di(p-methoxy cinnamate), (c) trimethylol ethane mono 2-ethylhexanoyl di(p-methoxy cinnamate), (d) glycerol mono 2-ethylhexanoyl di(o-methoxy cinnamate), (e) trimethylol propane mono 2-ethylhexanoyl di(o-methoxy cinnamate), (f) trimethylol ethane mono 2-ethylhexanoyl di(o-methoxy cinnamate) and the like.

The ultraviolet absorbing compounds according to the present invention can be prepared, for instance, from the esterification or ester interchange reaction of methoxy cinnamic acids or the derivative thereof, fatty acids having saturated branched alkyl groups of 7 carbon atoms or the derivative thereof and triols.

Examples of the methoxy cinnamic acids or the derivatives thereof used in the preparation of the ultraviolet absorbing compounds are o- and p-methoxy cinnamic acids and their esters (e.g. methyl ester, ethyl ester, propyl ester and the like), and the like. Para-methoxy cinnamic acid and methyl and ethyl esters thereof can be preferably employed in the preparation of the ultraviolet absorbing compounds.

Examples of the fatty acids having saturated branched alkyl groups of 7 carbon atoms or the derivatives thereof are 2-ethylhexanoic acid and its esters (e.g. methyl ester, ethyl ester, propyl ester and the like) and the like. The preferable fatty acids and the derivatives thereof are 2-ethylhexanoic acid and methyl and ethyl esters thereof and the like.

Examples of the triols employed in the preparation of the ultraviolet absorbing agents are glycerine, trimethylol propane, trimethylol ethane and the like.

The esterification reaction can be easily effected in the absence of or in the presence of any conventional esterification catalyst. The esterification catalysts optionally employed in the preparation of the ultraviolet absorbing compounds are, for example, sulfuric acid, hydrochloric acid, phosphoric acid, p-toluene sulfonic acid, sodium hydroxide, potassium hydroxide, sodium carbonate, potassium carbonate and the like. The reaction can be carried out, without using any solvent or in a solvent which forms an azeotropic mixture with water, such as, for example, toluene, xylene and the like, at a temperature of from approximately 130° to approximately 250° C., preferably from 160° to 220° C. When the reaction temperature is too low, the reaction rate becomes unpreferably slow. Contrary to this, when the reaction temperature is too high, the reaction products are remarkably discolored.

According to the present invention, since the fatty acid moiety in a liquid state at ordinary temperature is incorporated into the molecules of the ultraviolet absorbing compounds, the solidification of the compounds can be prevented and the compatibility of the compounds of the present invention with conventional base components or materials is remarkably improved, compared to the conventional ultraviolet absorbing agents containing, for example, the glycol diesters of p-methoxy cinnamic acid. The ultraviolet absorbing compounds of the present invention have an extremely high ultraviolet absorbing effect, as is clear from the high absorbance in the ultraviolet region in FIG. 1.

Furthermore, the ultraviolet absorbing compounds of the present invention have the feature that they can be safely applied to human skin without causing any skin irritation. This feature is very important, especially when they are incorporated as an ultraviolet absorbing agent into cosmetics. The safety test results of glycerol mono 2-ethylhexanoyl di(p-methoxy cinnamate) against animal skin are shown in Table I below.

TABLE 1

| Animal Skin Safety Test Item | Concentration of Test Compound in Acetone (W/V %) | Result | | |
|---|---|---|---|---|
| | | 24Hr | 48Hr | 72Hr |
| (1) Primary Irritation on Skin | 20 | 0 | 0 | 0 |
| | 50 | 0 | 0 | 0 |
| (2) Photo Toxicity | 5 | — | 0 | — |
| | 10 | — | 0 | — |
| | 20 | — | 0 | — |

TABLE 1-continued

| Animal Skin Safety Test Item | Concentration of Test Compound in Acetone (W/V %) | Result | | |
|---|---|---|---|---|
| | | 24Hr | 48Hr | 72Hr |
| (3) Contact Hyper Sensitivity | 10 | — | 0 | — |
| | 20 | — | 0 | — |
| | 50 | — | 0 | — |

(1) Primary Skin Irritation Test

Five healthy Hartley strain albino guinea pigs having a body weight of 300 through 500 g were used as test animals in this test. The backs of the five guinea pigs were shorn. The remaining fur on each guinea pigs' back was further removed by a depilatory cream containing thioglycolic acid and, then, the depilatory cream was washed and completely removed from the back of each of the albino guinea pigs. The guinea pigs were tested 24 hours after the depilatory treatment.

In this test, each guinea pig treated as mentioned above was immobilized in an animal holder and 0.05 ml of a sample to be tested was applied on a portion (having a size of 2×2 cms) of the back of the guinea pig. The skin irritation was examined 24, 48 and 72 hours after the application. The results were classified according to the following scale.

| No erythema | 0 |
|---|---|
| Slight erythema | 1 |
| Obvious erythema | 2 |
| Strong erythema | 3 |

As shown in Table I above, no primary skin irritation was observed in the five albino guinea pigs.

(2) Phototoxicity Test

This test was conducted according to a test method set forth on page 457, of "Environmental Toxicology: Method and Safety Evaluation", edited by Yasuhiko Shirasu et al and published by Soft Science Co., in Japan. In this test, five healthy Hartley strain albino guinea pigs were used as test animals and irradiation was conducted by using a Toshiba FL-40 BLB lamp. The total energy was $1.3 \times 10^8 erg/cm^2$. The results were determined 24 hours after the irradiation. The scale for classifying the results was the same as in the above-mentioned primary skin irritation test.

As shown in Table I above, no phototoxic reaction was observed in the five guinea pigs.

(3) Contact Hyper Sensitivity Test

This test was conducted according to a Magnusson B. and Kligman A. H. GPMT method (Guinea Pig Maximization Test) set forth in Fujio Morikawa et al, "Contact Hyper Sensitivity and Sensitizing Mechanism of the Sultones Contaminated in Alkylethoxy Sulfate Products", ALLERGY (27) 7, 1978. In this test, 20 healthy Hartley strain albino guinea pigs having a body weight of 300 through 500 g were used as test animals and the sensitizing treatment was effected by using the following liquids (A) and (B).

(A)

0.1 ml of FCA (Freund's Complete Adjuvant) Emulsion (available from Difco Laboratory, USA, $H_2O:FCA = 1:1$ V/V)

(B)

0.1 ml of a test sample solution (10 W/V % in acetone)

The liquids (A), (B) and a half amount of each of the liquids (A) and (B) were intradermally injected at the left and right shoulders 6 times each. After 1 week, a small amount of 10 W/V % sodium lauryl sulfate in vaseline was applied to each injected portion, and 24 hours later, a closed patch test was conducted by applying 0.2 ml of the test sample solution (10 W/V % in acetone) to each injected portion. After 48 hours, the closed patch was removed and the sensitizing treatment was completed.

After the above-mentioned treatment was completed, approximately 20 microliters of the test sample solutions containing various concentrations of the test compound in acetone were applied topically to the back skin of the sensitized animals. The results were determined according to the scale described in the primary skin irritation test (1). Sensitivity was evaluated by the number of the animals in which a positive reaction was observed. As is clear from the results shown in Table I above, so sensitivity was observed in the 20 albino guinea pigs.

As mentioned hereinbefore, since the ultraviolet absorbing compounds of the present invention are not only extremely effective as an ultraviolet absorbing agent, but also, can be very safely used, the amount of the compounds used as an ultraviolet absorbing agent may be varied over a wide range depending upon the intended use. Generally speaking, the present ultraviolet absorbing compound can be used in an amount of 0.1 through 15% by weight based on the weight of the material into which the ultraviolet absorbing compounds are incorporated.

The present invention now will be further illustrated by, but is by no means limited to, the following Examples, wherein all parts and percentages are expressed on a weight basis, unless otherwise noted.

EXAMPLE 1

Into a 500 ml flask, a mixture of 9.2 parts of glycerine, 39.2 parts of p-methoxy cinnamic acid, 15.8 parts of 2-ethylhexanoic acid and 10 parts of xylene was charged, and 0.5 parts of sodium hydroxide was added to the mixture. The resultant mixture was heated with stirring to a temperature of 180° through 200° C. The reaction was continued at this temperature range until the theoretical amount of water generated from the dehydration reaction was distilled off.

After the completion of the reaction, the reaction mixture was dissolved in ethyl ether and the insoluble substances were removed by filtration. The filtrate thus obtained was washed with a 5% aqueous solution of sodium hydroxide and, then, washed with water. After removing ethyl ether and xylene under a reduced pressure, the resultant liquid was decolorized by activated charcoal. Thus, a viscous oily product having a pale yellow color was obtained.

The ultraviolet light absorption spectrum data of the product (in ethanol solution) is as follows.

$\lambda max = 310$ nm.

$\epsilon$(Molecular Extinction Coefficient) = 45800.

The IR and NMR data of the product were as follows.

IR($\nu$max, cm$^{-1}$) = 1710, 1630, 1600, 1510.

NMR($\delta$, in CDCl$_3$) = 2.0~2.60(m, 1H), 3.77(S, 6H), 4.38(broad d, 4H, J=6 cps), 5.2–5.6(m, 1H), 6.23(d, 2H, J=15 cps), 6.81(d, 4H, J=8 cps), 7.38(d, 4H, J=8 cps), 7.60(d, 2H, J=15 cps).

EXAMPLE 2

To a mixture of 13.4 parts of trimethylol propane, 39.2 parts of p-methoxy cinnamic acid, 15.8 parts of 2-ethyl hexanoic acid and 10 parts of xylene, 0.5 parts of p-toluene sulfonic acid was added, and then, the mixture was heated with stirring to a temperature of 180° through 200° C. As the reaction proceeded, water which was generated from the reaction was removed, as an azeotropic mixture, from the reaction mixture. The reaction was continued until the theoretical amount of water was distilled off. After cooling, ethyl ether was added to the reaction mixture and the insolubles were removed by filtration. The filtrate was washed with a 5% aqueous solution of sodium hydroxide and, then, completely washed with water. Thereafter, ethyl ether and xylene were distilled off under a reduced pressure. The crude product thus obtained was decolorized with activated charcoal as described in Example 1 and a viscous oily product having pale yellow color was obtained.

The ultraviolet absorbing spectrum data is as follows.

$\lambda max = 310$ nm.

$\epsilon = 47600$.

The IR and NMR data of the product were as follows.

IR($\nu$max, cm$^{-1}$) = 1710, 1630, 1600, 1510.

NMR($\delta$, in CDCl$_3$) = 2.0~2.6(m, 1H), 3.77(S, 6H), 4.12(S, 2H), 4.20(S, 4H), 6.22(d, 2H, J=16 cps), 6.80(d, 4H, J=8 cps), 7.38(d, 4H, J=8 cps), 7.58(d, 2H, J=16 cps).

EXAMPLE 3

A mixture of 9.2 parts of glycerine, 45.4 parts of ethyl p-methoxy cinnamate, 18.9 parts of ethyl 2-ethylhexanoate and 0.5 parts of potassium carbonate were heated to a temperature of 170° through 180° C., while nitrogen gas was bubbled through the mixture. The reaction was continued at said temperature range, until the theoretical amount of the ethyl alcohol generated from the reaction was distilled off. After that, the reaction mixture was washed with n-hexane several times at a temperature of approximately 50° C., and then, dissolved in ethyl ether. The solution thus obtained was washed with a 5% aqueous solution of sodium hydroxide and, then, with water. After drying, the ethyl ether was distilled off under a reduced pressure. Thus, a viscous oily product having pale yellow color was obtained.

The ultraviolet absorbing spectrum data of the product is as follows.

$\lambda max = 310$ nm.

$\epsilon = 45800$.

The IR and NMR data of the product were identical to those of the product obtained in Example 1.

EXAMPLE 4

To a mixture of 9.2 parts of glycerine, 39.2 parts of o-methoxy cinnamic acid, 15.8 parts of 2-ethylhexanoic acid and 10 parts of xylene, 0.5 parts of sodium hydroxide was added and, then, the mixture was heated with stirring to a temperature of 180° through 200° C. The reaction was continued until the theoretical amount of water was azeotropically distilled off. An oily product having a pale yellow color was obtained in the manner as described in Example 1.

The analytical data of the product is as follows.
UV Absorbing Spectrum.
$\lambda max = 325$ nm, $\epsilon = 21000$.
IR($\nu max^{kBr}$, cm$^{-1}$) = 1710, 1625, 1600, 1490.
NMR($\delta$, in CDCl$_3$) = 2.1~2.5(m, 1H), 3.8(S, 6H), 4.4(bd, 4H), 5.3~5.7(m, 1H), 6.50(d, 2H, J=16 cps), 7.99(d, 2H, J=16 cps) 6.7~7.6(complex signals of Aromatically bound hydrogen, 8H).

EXAMPLE 5

The ultraviolet light protective property of the present ultraviolet absorbing agent was evaluated by using the compound prepared in Example 1 above.

In the tests, water in oil (w/o) emulsion type compositions containing and not containing the compound prepared in Example 1 and oil type compositions containing and not containing the compound prepared in Example 1 were used as test samples. The compositions of these samples were as follows.

| W/O Emulsion Type Sample | | |
|---|---|---|
| Composition | Sample A | Sample B |
| Vaseline | 10.0% | 10.0% |
| Microcrystaline Wax | 5.0 | 5.0 |
| Solid Paraffin | 5.0 | 5.0 |
| Squalane | 40.0 | 40.0 |
| Beeswax | 10.0 | 10.0 |
| Polyoxyethylene Sorbitol Monolaurate | 1.0 | 1.0 |
| Sorbitan Sesquioleate | 5.0 | 5.0 |
| Deionized Water | 21.0 | 24.0 |
| Compound prepared in Example 1 | 3.0 | — |

| Oil Type Sample | | |
|---|---|---|
| Composition | Sample C | Sample D |
| Liquid Paraffin | 60.0% | 63.0% |
| Olive Oil | 37.0 | 37.0 |
| Compound prepared in Example 1 | 3.0 | — |

The tests were conducted by applying these samples A, B, C and D to back skins of Hartley strain albino guinea pigs as follows.

The fur on the backs of two groups of guinea pigs each consisting of 5 guinea pigs was removed in a day before the test being conducted. The surface of the back of each of the treated guinea pigs was longitudinally divided into three portions with light non-transmittable plaster. The left and right portions each having a size of 2×9 cm$^2$ thus divided were uniformly coated with the test sample at a coating coverage of 2 microliter/cm$^2$ and no coating was applied to the central portion, which was a control portion. After that, the surface of the back of each of the guinea pigs was laterally divided to six portions with light non-transmittable plaster. Thus, 18 slots in total were prepared in the back of each of the guinea pigs. The size of each slot was 3 cm$^2$.

Each slot was irradiated for various irradiation periods of time by using a Toshiba fluorescent lamp FL-40SE ($\lambda max$ 307 nm). The distance between the slot surface and the lamp was 30 cm.

The results were determined 24 hours after the irradiation. The ultraviolet light protective property was evaluated according to a protection factor P.F., which was calculated as follows.

$$PF = Ts/Tc$$

wherein Ts is a minimum irradiation time causing slight erythema in the coated portion and Tc is a minimum irradiation time causing slight erythema in the non-coated control portion.

The result, on average, of each sample is shown in the following table.

TABLE

| Sample | P.F. |
|---|---|
| A | 4.3 |
| B | 1.2 |
| C | 1.4 |
| D | 1.0 |

We claim:

1. An ultraviolet absorbing agent for human skin comprising at least one compound having the following general formulae

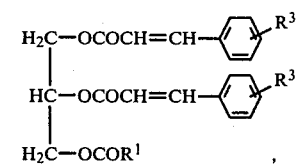

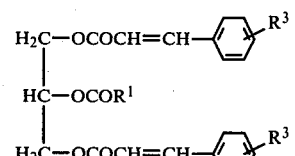

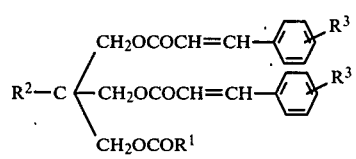

wherein $R^1$ is a saturated branched alkyl group having 7 carbon atoms, $R^2$ is a methyl or ethyl group and $R^3$ is an ortho- or para- methoxy group.

2. An ultraviolet absorbing agent according to claim 1, wherein said compound is derived from the esterification or ester interchange reaction of methoxy cinnamic acid or the derivative thereof, fatty acids having saturated branched alkyl groups of 7 carbon atoms or the derivative thereof and triols.

3. An ultraviolet absorbing agent according to claim 2, wherein said compound is derived from the esterification reaction of p-methoxy cinnamic acid, 2-ethylhexanoic acid and glycerine.

4. An ultraviolet absorbing agent according to claim 2, wherein said compound is derived from the esterification reaction of p-methoxy cinnamic acid, 2-ethylhexanoic acid and the trimethylol propane.

5. An ultraviolet absorbing agent according to claim 2, wherein said compound is derived from the esterification reaction of ethyl p-methoxy cinnamate, ethyl 2-ethylhexanoate and glycerine.

6. An ultraviolet absorbing agent according to claim 1, wherein said compound is glycerol mono 2-ethylhexanoyl di(p-methoxy cinnamate).

7. An ultraviolet absorbing agent according to claim 1, wherein said compound is trimethyl propane mono 2-ethylhexanoyl di(p-methoxy cinnamate).

8. An ultraviolet absorbing agent according to claim 1, wherein said compound is glycerol mono 2-ethylhexanoyl di(o-methoxy cinnamate).

9. A method of protecting human skin from erythema inducing ultraviolet radiation which comprises applying to the skin an effective amount of a composition containing an effective amount of at least one compound having the following general formulae:

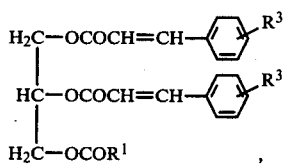

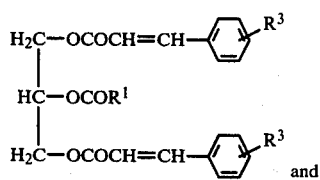
and

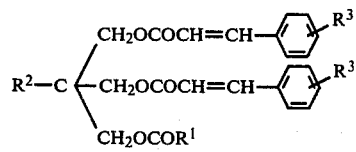

wherein $R^1$ is a saturated branched alkyl group having 7 carbon atoms, $R^2$ is a methyl or ethyl group and $R^3$ is an ortho- or para- methoxy group.

10. The method according to claim 9, wherein said compound is derived from the esterification or ester interchange reaction of methoxy cinnamic acid or the derivative thereof, fatty acids having saturated branched alkyl groups of 7 carbon atoms or the derivative thereof and triols.

11. The method according to claim 10 wherein said compound is derived from the esterification reaction of p-methoxy cinnamic acid, 2-ethylhexanoic acid glycerine.

12. The method according to claim 10, wherein said compound is derived from the esterification reaction of ethyl p-methoxy cinnamate, ethyl 2-ethylhexanoate and glycerine.

13. The method according to claim 10, wherein said compound is derived from the esterification reaction of ethyl p-methoxy cinnamate, ethyl 2-ethylhexanoate and glycerine.

14. The method according to claim 9, wherein said compound is glycerol mono 2-ethylhexanoyl di(p-methoxy cinnamate).

15. The method according to claim 9, wherein said compound is trimethyl propane mono 2-ethylhexanoyl di(p-methoxy cinnamate).

16. The method according to claim 9, wherein said compound is glycerol mono 2-ethylhexanoyl di(o-methoxy cinnamate).

* * * * *

UNITED STATES PATENT AND TRADEMARK OFFICE
CERTIFICATE OF CORRECTION

PATENT NO. : 4,322,544
DATED : March 30, 1982
INVENTOR(S) : Tomomi Okazaki et al It is certified that error appears in the above-identified patent and that said Letters Patent is hereby corrected as shown below:

On the Title page Assignee Item [73] should read :

-- SHISEIDO COMPANY LTD. --.

Signed and Sealed this

Tenth Day of August 1982

[SEAL]

Attest:

Attesting Officer

GERALD J. MOSSINGHOFF
Commissioner of Patents and Trademarks